US00PP26871P3

(12) United States Plant Patent
Gradziel et al.

(10) Patent No.: US PP26,871 P3
(45) Date of Patent: Jun. 28, 2016

(54) PEACH TREE NAMED 'KADER'

(50) Latin Name: *Prunus persica*
Varietal Denomination: Kader

(71) Applicant: The Regents of the University of California, Oakland, CA (US)

(72) Inventors: Thomas M. Gradziel, Davis, CA (US); Mary Ann Thorpe, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 113 days.

(21) Appl. No.: 14/120,717

(22) Filed: Jun. 18, 2014

(65) Prior Publication Data

US 2015/0373887 P1 Dec. 24, 2015

(51) Int. Cl.
*A01H 5/08* (2006.01)

(52) U.S. Cl.
USPC ..... Plt./197

(58) Field of Classification Search
USPC ..... Plt./197
See application file for complete search history.

(56) References Cited

PUBLICATIONS

The Jan. 1, 2009 Test Agreement for Trees/Rootstocks between Harvinder Kullar and the Regents of the University of California, 7 pages.
The Jan. 1, 2009 Test Agreement for Trees/Rootstocks between Paul Rai and the Regents of the University of California, 7 pages.
The Feb. 11, 2009 Test Agreement for Trees/Rootstocks between Wil Sohal and the Regents of the University of California, 7 pages.
The Feb. 20, 2009 Test Agreement for Trees/Rootstocks between Sean Carberry and the Regents of the University of California, 7 pages.
The Jun. 1, 2009 Test Agreement for Trees/Rootstocks between Dave Wilson Nursery, Inc. and the Regents of the University of California, 7 pages.

*Primary Examiner* — Annette Para
(74) *Attorney, Agent, or Firm* — Morrison & Foerster LLP

(57) ABSTRACT

A new peach variety (*Prunus persica*) designated as 'Kader' is provided. 'Kader' forms attractive, high quality fruit that matures approximately six to ten days earlier than that of the 'Andross' variety and demonstrates a capacity to maintain good on-tree fruit quality for up to one week, allowing delayed harvest and economically efficient single harvests. Further, 'Kader' fruit exhibits the desirable characteristic of being free from the red staining of the pit area of fruit flesh resulting from anthocyanin formation, while still exhibiting other fruit characteristics that are believed to be substantially similar to those of the commercially important 'Carson' and 'Andross' peach varieties.

4 Drawing Sheets

Latin name: Botanical/commercial classification: *Prunus persica* new peach cultivar.

Varietal denomination: The varietal denomination of the claimed peach variety is 'Kader'.

BACKGROUND OF THE INVENTION

An objective of processing peach breeding programs is to develop new peach varieties that are commercially desirable. In particular, there is a need for the development of new peach varieties that are suitable replacements for the 'Early' maturity season varieties 'Dixon' and 'Andross', and the 'Late' season variety 'Halford' (each non-patented in the United States).

Peach variety 'Dixon' originated in Linden, Calif., by F. A. Dixon, of the Canners League of California in San Francisco and was introduced in 1956. 'Dixon' trees produced very high yields, which made this variety popular for growers. While 'Dixon' fruit flesh was a desirable yellow-gold, the pit often exhibited a pink to red color from the formation of red anthocyanins. This red color oxidizes to brown when canned, resulting in an undesirable fruit color as well as an undesirable brown staining of canned syrup. The red stained fruit stone or endocarp is also more prone to breakage, resulting in pit fragments being left with the fruit flesh during processing. As result of these problems, processors stopped purchasing 'Dixon' fruit from growers. Although the 'Dixon' variety is no longer commercially planted, no replacement variety presently exists.

Peach variety 'Andross' was developed as a source of fruit for processors during the early 'Early' maturity season following 'Dixon' production. 'Andross' originated in Davis, Calif., by L. D. Davis, Department of Pomology, University of California, Davis and was introduced in 1964. 'Andross' trees consistently set heavy crops, have leaves with globose glands, and flowers of the larger non-showy type. Although 'Andross' is the most heavily planted variety for the 'Early' maturity season, this variety also produces fruit with red-staining of the pit and associated higher frequencies of endocarp (stone) fragments remaining in processed flesh. Consequently, processors are no longer encouraging new plantings of this variety, and indicate that they may no longer purchase fruit of this variety in the future. As a result, there is a need to develop new peach varieties having desirable fruit characteristics. The new peach variety 'Kader' as described herein is a product of this breeding effort.

SUMMARY OF THE INVENTION

The present disclosure relates to a new and distinct peach cultivar (*Prunus persica*) that has been denominated as 'Kader' and more particularly to such a peach variety that lacks the undesirable red-staining of the pit in the peach fruit. 'Kader' fruit ripens during the commercially important 'Dixon' period between ripening of the 'Carson' and 'Andross' fruits. In addition to the desirable ripening period of 'Kader', this variety has processing clingstone fruit that remains free from the anthocyanin red pit staining, as occurs in 'Dixon' and 'Andross'. 'Kader' fruit is large in size, being slightly angular to round in shape and with a slight fruit tip, and having fruit flesh that is bright golden-yellow. Good on-tree fruit quality of the present variety is maintained for up to one week following initial ripening, allowing for delayed and once-over harvest. 'Kader' fruit skin is slightly less fuzzy than that of 'Andross', with a more uniform golden-yellow color. The fruit pit of 'Kader' is medium in size and the tree is upright-spreading and with slightly more vigor than observed in 'Andross'. The 'Kader' crop is similar to 'Andross' and higher than 'Carson' under commercial conditions, having higher processer case-yields resulting from lower pit fragments and absence of the red pit staining common to 'Dixon' and 'Andross' varieties.

Peach variety 'Kader' was originally identified as selection '90,9-116' and was isolated from a seedling population obtained from a cross between 'Ross' and 'R1-1' peach varieties. Based on its promising performance, particularly its attractive and high-quality fruit, absence of red staining in the pit area of fruit flesh, and capacity to maintain good on-tree fruit quality for up to one week, selection '90,9-116' was selected as a candidate for release as the variety 'Kader'.

BRIEF DESCRIPTION OF THE TABLES

TABLE 1 shows various fruit characteristics of the 'Kader' peach relative to other commercial standard varieties. Values presented are averages of data collected over three years from fruit randomly collected from eight 6-year-old trees planted in Davis, Calif. research plots. Trees were heavily thinned to less than one fruit per 50 cm bearing shoot to minimize competition effects.

TABLE 2 shows fruit Brown-rot disease scores for 'Kader' peach and other peach varieties following controlled lab inoculations and incubations. Values presented are three year averages.

TABLE 3 shows polyphenol oxidase (PPO) activity and associated fruit flesh bruising/browning values for 'Kader' peach and other peach varieties following controlled lab incubations.

TABLE 4 shows fruit flesh firmness (lbs.) values for 'Kader' and 'Dixon' varieties at tree-ripe stage and seven days after tree-ripe. Firmness below 6 lbs. is considered too soft for canning. "STD" values represent standard deviation.

DETAILED DESCRIPTION OF THE INVENTION

Figure 4:
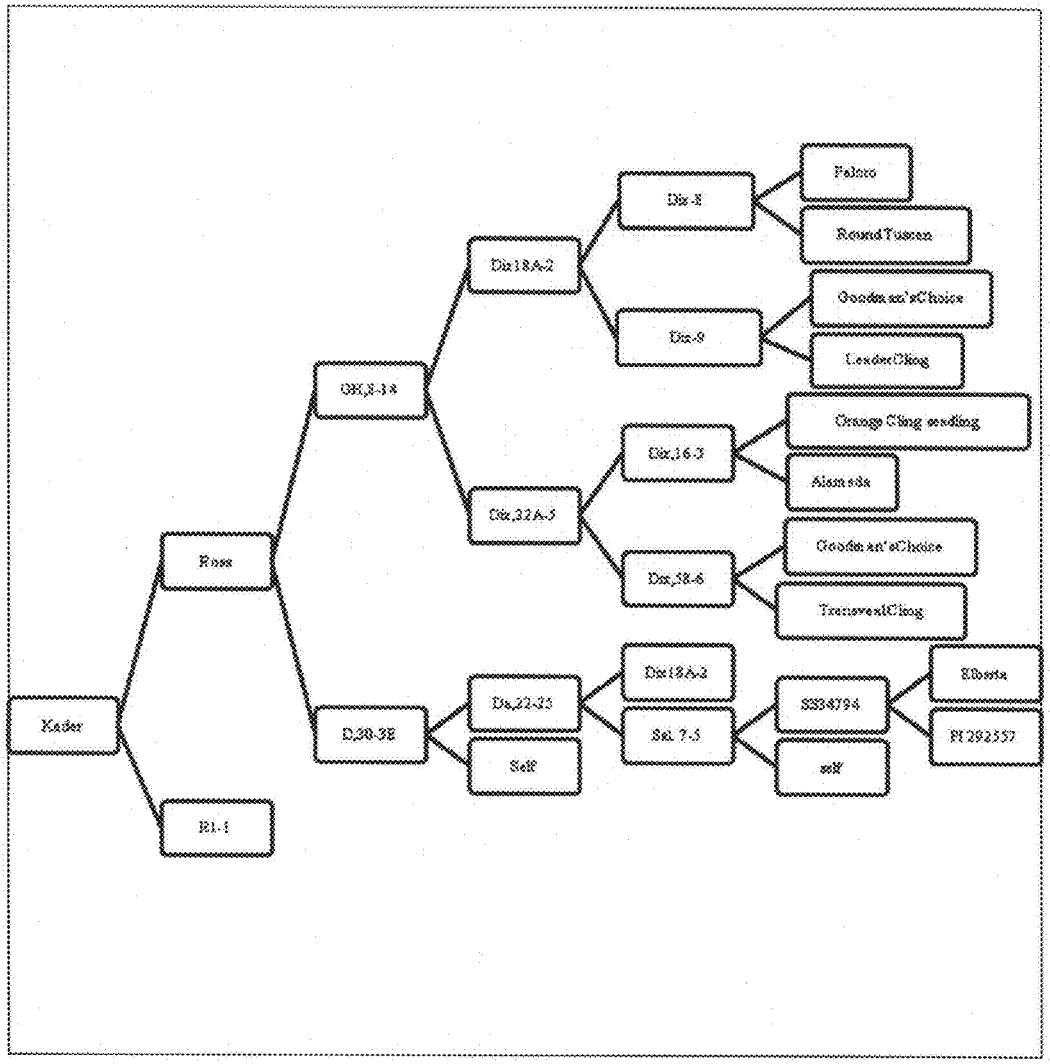
FIG. 4 illustrates the breeding pedigree of peach variety 'Kader'.

The detailed breeding pedigree of peach variety 'Kader' is presented in FIG. 4. The original seedling population from which peach variety 'Kader' was selected was produced by a controlled cross made during Year 1 between the University of California (UC) processing peach variety 'Ross' as the female (seed) parent and the UC processing peach breeding line 'R1-1' as the male (pollen) parent. A total of seven seedlings were recovered from this cross and planted in Year 2. The 'Kader' seedling, which was given an initial individual seedling designation number of '90,9-116', was grown along with many other seedlings in the D6C,90-block at the University of California, Davis in Year 2. Fruit from the original '90,9-116' seedling was first evaluated in Year 4, with continued evaluations of trees and canned samples from Year 4 to Year 25. The original '90,9-116' tree was removed from the initial D6C,90-block at Davis, Calif. during Year 5, but this variety was asexually propagated (via the T-budding method of grafting) onto 'Lovell' peach rootstock and has been maintained in an advance selection block at the Wolfskill Experimental Orchards in Winters, Calif. since that time.

Following the initial Year 4 evaluations, in Year 13, selection '90,9-116' ('Kader') was selected for additional evaluation based on its good fruit and tree qualities, the absence of red staining of the pit of the peach fruit, and its desirable ripening time being similar to peach variety 'Dixon'. '90,9-116' was then subsequently propagated and placed into regional test plantings in Wolfskill Experimental Orchards in Winters, Calif. at the Davis Pomology Field Facilities, and at the Kearney Agricultural Center at Parlier, Calif. All propagated trees of this new variety produced fruit in the Year 15 season, and all fruit was true-to-type to the original seedling evaluated during Year 4. Based on promising results, additional grower evaluation plots were established in Year 16 for '90,9-116' in the Sacramento and San Joaquin Valleys of California under the individual seedling designation of 'Extra-Early #1'.

Field test evaluations through Year 25 confirm earlier-established desirable characteristics of the present variety and indicate substantial commercial potential for the new variety 'Kader'. Sacramento Valley grower yields in Year 23 and Year 24 for peach variety 'Kader' were above 15 T/H for both years, being comparable to the adjacently planted 'Early'-season 'Andross' variety. Further, grower yields for 'Kader' were consistently 1 T/H above the adjacent 'Extra-Early' season cultivar 'Carson', while also displaying desirable fruit quality (TABLE 1). Tree-ripe fruit of 'Kader' also demonstrate the capacity to maintain good quality for over 1 week on-the-tree (TABLE 4). This allows for delayed harvest and economically efficient once-over harvest, including mechanical-harvest, rather than multiple hand-harvests which are currently being practiced for other peach varieties currently being used. Improved resistance to Monilinia fruit brown rot (TABLE 2) and resistance to flesh browning/bruising (TABLE 3) also contribute to very good delayed-harvest and post-harvest quality. The exceptional fruit-sizing capacity of 'Kader', combined with good mature fruit organoleptic quality and firmness (TABLE 1), allow interior and otherwise retarded fruit to continue to size with delayed harvest, further contributing to a high yield potential.

'Kader' peach is primarily a nonmelting clingstone peach that would primarily be grown and sold as a processing fruit rather than as a fresh market fruit. The most comparable example of this type of processing clingstone peach is the 'Andross' clingstone peach variety. In California, the 'Andross' variety is grown only for processing, and the acreage of 'Andross' in California at the present time is approximately 4,000 acres. The 'Kader' clingstone peach is targeted at the same processing market as 'Andross', and it is thought that 'Kader' is especially commercially attractive as a variety which produces fruit during the critical 'Dixon' harvest period. Currently, no other clingstone peach matures in the season of 'Kader', and no other processing clingstone peach of this fruit ripening or maturity season lacks red staining of the pit. Lack of pit staining is an especially attractive feature for peach processors.

BOTANICAL DESCRIPTION OF THE PLANT

The following is a detailed horticultural description of the new peach cultivar 'Kader' obtained from asexually propagated (via vegetative propagation using the T-budding method of grafting onto 'Lovell' rootstock) progeny observed during the Year 23 and Year 25 growing seasons. The following tree descriptions are based on 12-years-old trees, unless otherwise indicated. Tree descriptions were subsequently verified on younger trees (trees between 6-years-old and 12-years-old). The trees were grown at the Wolfskill Experimental Orchards of the University of California located at Winters, Calif. and at the University of California Research Plots at Davis, Calif. Color designations are presented with reference to the "Dictionary of Color" by Maerz and Paul, First Edition (1930).

Botanical classification: *Prunus persica*, cv. 'Kader'.

Tree characteristics:

*Size*.—Medium. Trees resulting from an asexual propagation of 'Kader' during Year 22 had a height of approximately 3.5 meters and a breadth of approximately 3.7 meters across the crown when trained to four scaffolds.

*Vigor*.—Medium. Trees produced approximately 0.6 to 1.0 meter of new growth during the Year 25 growing season.

*Growth habit*.—Spreading to upright-spreading.

*Hardiness*.—Hardy under typical Sacramento Valley climatic conditions.

*Production*.—Productive.

*Bearing*.—Regular bearer.

Trunk characteristics:

*Size*.—Medium to large. The trunk diameter at 10 cm above the ground is approximately 23 to 25 cm. The scaffold diameters at the base of the scaffolds are approximately 14 cm.

*Texture*.—Relatively coarse with substantial scarfskin.

*Color*.—The bark color ranges from brown-grey (15-A-4 Quail Brown) to more medium brown (8-C-8 Chaeture Brown).

*Lenticels*.—Numerous, large, flattened and generally oval-shaped. Typically the lenticels range from approximately 2 to 5 mm in width at a right angle to the trunk and are approximately 0.5 to 2 mm in height. The lenticel surface is light brown in coloration (13-I-11 Sorrel) and is moderately calloused.

Branch characteristics:

*Size*.—Medium.

*Texture*.—Medium.

*Color*.—Mature shoots are light brown (14-C-8 Mocha Bisque) to darker brown (7-C-10 Brownstone). Shoots from the Year 25 growing season are pale light green (20-L-4). The exposed surfaces are commonly tinged rose-red (7-E-6 Canyon). The coloration of the new expanding shoot tips is yellow green (20-L-7).

*Lenticels*.—Somewhat linear at a right angle to the shoots, and light in coloration.

*Internode length*.—Hanger shoots from the Year 25 growing season have a length between nodes that is commonly approximately 15 to 32 mm.

Leaf characteristics

*Size*.—Medium to large. Typical length from vigorous leaves from Year 25 growing season is approximately 15 to 18 cm including the petiole, and typical width is approximately 3.5 to 5 cm. The leaf thickness is average.

*Form*.—Lanceolate.

*Apex*.—Acuminate and often curves downward.

*Aspect*.—The blade commonly ranges from substantially flat to somewhat folded upwards.

*Color*.—The upper surface is dark green (23-J-7) and the lower surface is a much lighter grey-green (22-L-8). The primary and mid-vein on the under surface is pale yellow-green (17-H-1).

*Margin*.—Crenate and occasionally double crenate. The crenations are relatively large and uniform. The leaf margins commonly range from straight to moderately undulate.

*Petiole*.—Generally medium in size, commonly approximately 8 to 15 mm in length, approximately 2 mm in thickness, and pale yellow-green lower surface (18-J-6).

*Glands*.—Small to medium in size, almost always globose, alternate, commonly 1 to 2 on the petiole, often borne on a short stalk, and frequently 0 to 2 additional glands can be observed at the base of the leaf blade. The coloration is shiny light green-yellow (18-J-2), occasionally developing a reddish tinge with age.

*Stipules*.—Linear lanceolate in configuration, most are early deciduous, margins are serrate, commonly approximately 6 to 9 mm in length, and the coloration of young stipules commonly is light green-yellow (17-K-4) with darkening to brownish upon aging.

Fruit characteristics:

*Maturity when described herein*.—Full commercial maturity.

*Picking*.—First pick was July 15 of Year 25, and last pick was August 1 of Year 25.

Figure 1:
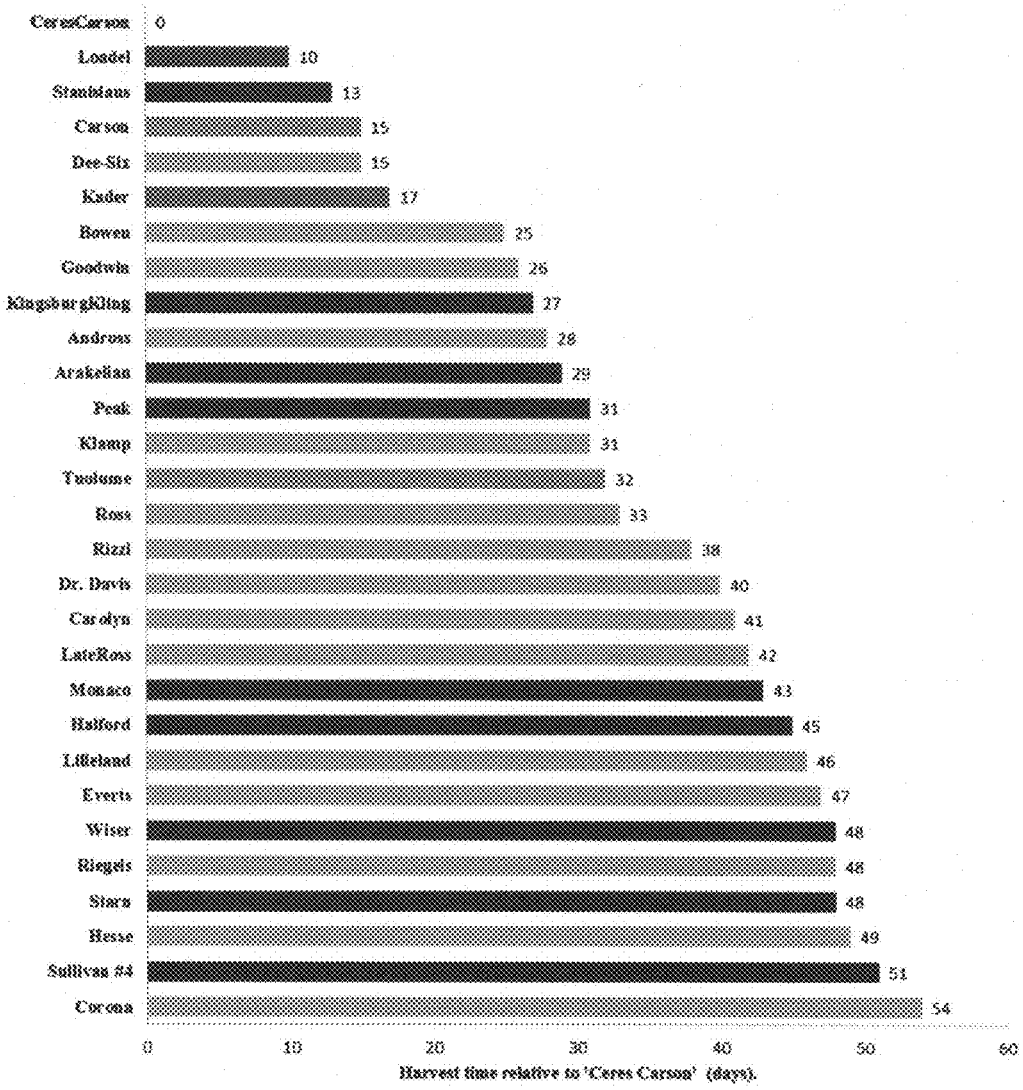
FIG. 1 illustrates the maturity sequence of California processing peach varieties. The new cultivar 'Kader' ripens between 'Carson' and 'Bowen' in the gap left by the loss of the cultivar 'Dixon'. X-axis values indicate the average ripening time (days) after 'Ceres Carson'. Orange bars are peach varieties released by the University of California, green bars are private breeder releases, and all other bars are chance grower selections.

*Season of maturity*.—Between the 'Carson' and 'Andross' cultivars (See FIG. 1).

Figure 3:
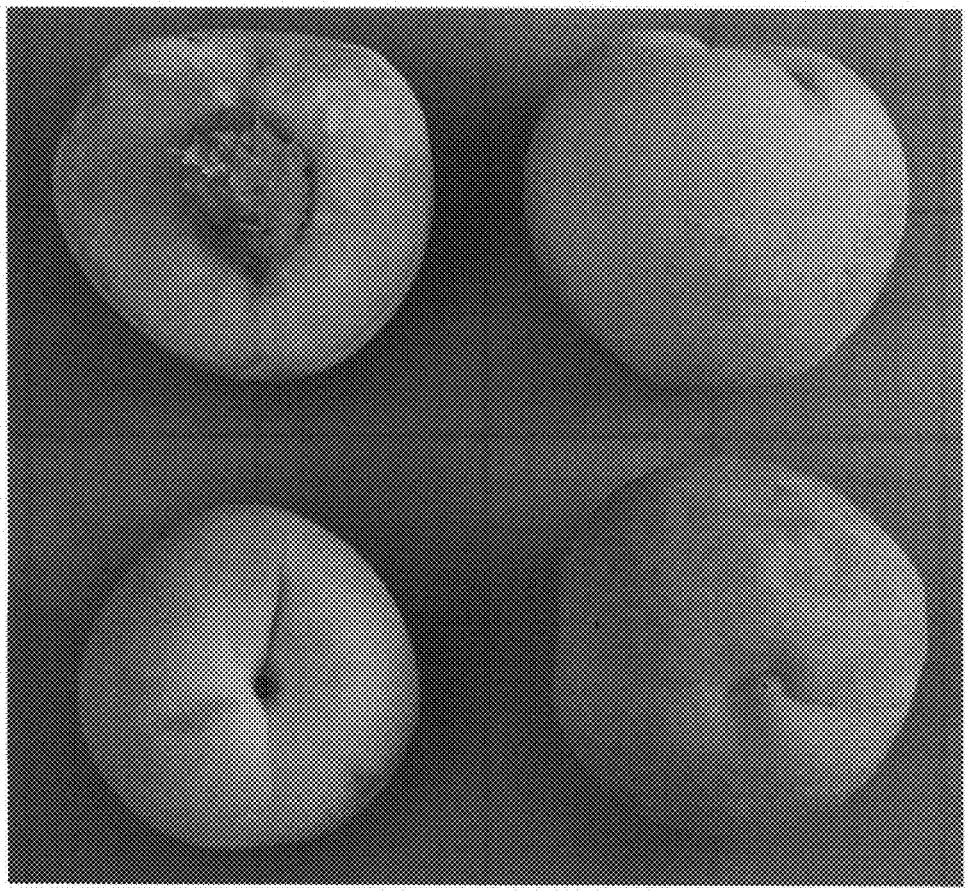
FIG. 3 illustrates fruit of the 'Kader' peach variety under commercial thinning rates (small square grids are 1 $cm^2$).

*Size*.—Uniform, large. Average axial diameter is approximately 81 mm, average suture diameter is approximately 88 mm, and the average cheek diameter is approximately 92 mm when highly thinned. Images of the 'Kader' peach fruit are presented in FIG. 3.

*Form*.—In lateral aspect the fruit is globose to slightly oblate in form. In apical aspect the fruit is nearly globose with slight variability.

*Suture*.—Inconspicuous line and slightly deeper at base and at apex.

*Ventral surface*.—Rounded and slightly lipped at base.

*Base*.—Rounded. Base angle variable from right angle to oblique.

*Stem cavity*.—Broad and moderately deep.

*Apex*.—Generally rounded with a low and occasionally angled tip. Pistil point is usually apical. Slight depression is present on dorsal suture next to the apex.

*Pistil point*.—Most frequently oblique.

*Stem length and thickness*.—Medium.

*Skin pubescence*.—Pubescent with a fine, short, matted pubescence. No observed tendency to crack.

*Skin color*.—The primary ground color is a uniform orange-yellow (10-J-6). The fruit surface has a moderate amount of blush coloration present, from 20% to 60% of the total surface. Fruits exposed to direct sunlight usually have the highest percent blush. The blush pattern is primarily washed with a moderate amount of dark mottling present. The blush color ranges from a dark garnet red (7-H-4) to a lighter shade of red (5-L-1) with a range of variation in between.

*Flesh color*.—A uniform golden-yellow from skin to stone cavity (10-L-6).

*Flesh texture*.—Fine and non-melting.

*Flesh fibers*.—Few in number, short and fine.

*Ripening*.—Ripens evenly.

*Flavor*.—High quality.

*Aroma*.—Moderate, pleasant.

*Eating quality*.—Good.

*Canning quality*.—Very good.

*Stone type*.—Clingstone with flesh connected over the entire stone surface.

*Stone size*.—Medium. Average mass for highly thinned fruit is 25 g, or approximately 15% of total fresh fruit mass.

*Fibers*.—Numerous very short and fine fibers present, attached laterally to the stone.

*Form*.—Variable but most often slightly ovate.

*Base*.—Moderately narrow and medium truncate in form. Base angle is variable but most often slightly oblique to the stone axis.

*Stone hilum*.—Medium in size and well defined. Hilum form is oval.

*Apex*.—Apex form is generally rounded with a broad, rather blunt tip.

*Stone side*.—Variable but most often nearly equal.

*Stone surface*.—Moderately coarse with the heaviest grooving near the ventral suture running nearly parallel to the suture.

*Ventral edge*.—Medium in width with several low wings. Wings are most prominent from mid-suture to the stone base.

*Dorsal edge*.—Somewhat variable in form, but most often the dorsal suture is moderately narrow.

*Stone color*.—When dry, light hazel-brown (13-D-8).

*Tendency to split*.—Low.

Flower characteristics:

*Chilling season*.—Low to medium for growing location. There were approximately 900 to 1,100 chilling hours at temperatures below 45° F. for the Year 22 to Year 25 winter seasons.

Figure 2:
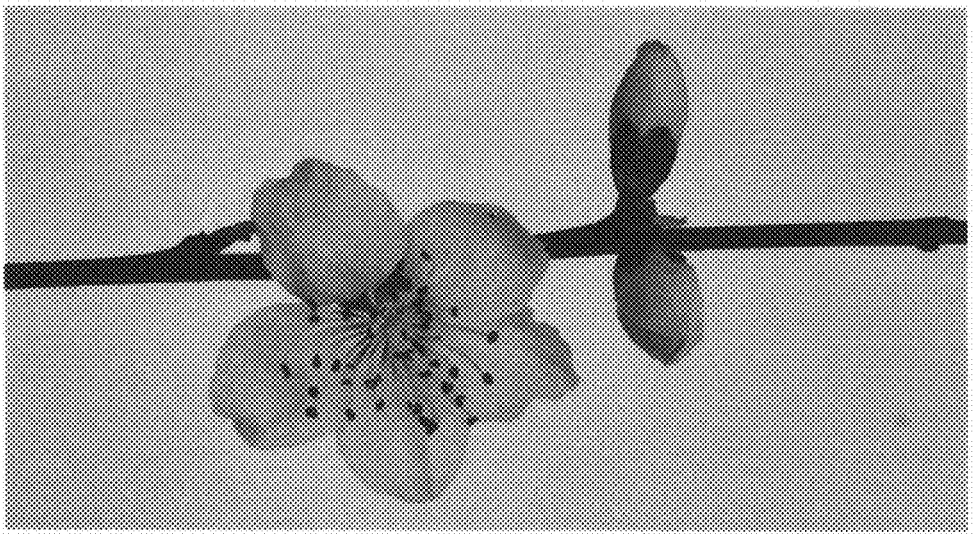
FIG. 2 illustrates open flower and closed flower buds of the 'Kader' peach variety.

*Buds*.—Medium to large in size, conic in form, plump, free of stem, with moderately pubescent surfaces of a light grey coloration. The exterior bud scale ranges from grey (15-A-6 Beaver Grey) to grey-brown (15-A-8 Winter Leaf Brown) in coloration. The buds are hardy under typical climatic conditions of the Sacramento Valley. There commonly are one to two floral buds per node. Images of the 'Kader' flower and closed buds are presented in FIG. 2.

*Bloom timing*.—Mid-season in relation to other commercial cling peach cultivars. During Year 23 and Year 24, bloom periods were similar to the 'Andross' cultivar.

*Size*.—The flower size is large and showy. The fully expanded flower diameter commonly is approximately 30 to 44 mm.

*Bloom quality*.—Commonly abundant throughout the tree. Frequently two flowers per node.

*Petals*.—The petal size is large and commonly ranges from approximately 14 to 21 mm in length and from approximately 12 to 18 mm in width. The petal number is five. The petal form is oblong. The young petals are light pink (1-C-1) and darken slightly at maturity (1-D-3). The petal claw is moderately large and truncate in form. The claw color is dark rose-pink (1-I-5) and darker than the overall petal. The petal margins are lightly ruffled. The petal apices are variable, most frequently rounded though sometimes obtuse or with a slight depression at apex.

*Pedicel*.—Quite short and commonly exhibits a length of approximately 1 to 1.5 mm and a thickness of approximately 1 to 1.5 mm. The coloration is bright green (17-K-4) and the surface is glabrous.

*Nectaries*.—Bright orange (9-D-12) at maturity.

*Calyx*.—Glabrous and quite rugose, and the coloration is maroon (7-L-7) at maturity.

*Sepals*.—Pubescent with greyish tinge, average in size, conic in form, and maroon (6-K-4 to 6-J-5) in coloration and approximately 5 mm in length and 4 mm in width.

*Anthers*.—Average in size, dark red dorsally (5-L-8) and tan-red ventrally (4-A-10).

*Stamens*.—Variable in length and commonly range from approximately 12 to 18 mm in length. Frequently extend above the pistil. The filaments are very pale pink when young (1-B-1) and become dark maroon (3-J-4) with advancing maturity. Average number is 25-35.

*Pollen*.—Abundant and yellow-gold (10-K-6) in coloration.

*Pistil*.—Pubescent basally over the ovary, and much less so near the stigma and upper style area. The length commonly is approximately 12 to 15 mm including the ovary. The coloration is pale green (17-I-1) over the upper style area.

Miscellaneous characteristics:

*Major use*.—Canning.

*Keeping quality*.—Good.

*Resistance to insects and diseases*.—Low susceptibility to *Monilinia* brown rot, otherwise average.

TABLE 1

Fruit Characteristics

| Item | CIELAB color a* | CIELAB color b* | CIELAB color L* | Brix | TA | Brix/TA |
|---|---|---|---|---|---|---|
| Loadel | 5.7 a | 48.6 ab | 70.8 a | 8.0 a | 0.5 ab | 16.8 |
| Carson | 5.0 a | 50.8 b | 71.5 a | 7.5 a | 0.4 a | 17.0 |

TABLE 1-continued

| Fruit Characteristics | | | | | | |
|---|---|---|---|---|---|---|
| Kader | 7.0 ab | 45.0 ab | 77.2 ab | 12.5 c | 0.5 ab | 25.7 |
| Dixon | 6.1 ab | 41.4 a | 76.4 ab | 12.3 c | 0.4 a | 30.2 |
| Goodwin | 9.1 b | 44 a | 75.5 ab | 12.7 c | 0.6 b | 22.6 |
| Andross | 6.9 ab | 45.9 ab | 78.1 ab | 12.4 c | 0.4 a | 30.5 |
| Klampt | 5.4 a | 46 ab | 78.7 ab | 10.7 ab | 0.5 ab | 21.6 |
| Ross | 5.3 a | 43.3 a | 79.7 b | 10.8 ab | 0.5 ab | 22.5 |
| DrDavis | 7.2 ab | 45.5 ab | 78.8 ab | 11.8 abc | 0.5 ab | 22.3 |

| Item | pH | Fruit weight (g) | Fruit flesh firmness (lbs) | Maturity (d after Loadel) | Red in pit |
|---|---|---|---|---|---|
| Loadel | 3.8 a | 183.7 a | 6.1 ab | 0 | (−) |
| Carson | 4.0 a | 219.5 ab | 5.2 ab | 5.3 | (−) |
| Kader | 4.0 a | 332.7 bc | 6.9 b | 7.2 | (−) |
| Dixon | 4.1 a | 226.4 ab | 4.4 a | 10.6 | (+) |
| Goodwin | 3.9 a | 236.2 ab | 7.8 bc | 15.9 | (-) |
| Andross | 4.1 a | 332.2 bc | 7.5 bc | 17.7 | (+) |
| Klampt | 3.9 a | 353.1 c | 5.4 ab | 20.3 | (−) |
| Ross | 3.8 a | 236.1 ab | 8.2 c | 23.8 | (−) |
| DrDavis | 3.9 a | 320.1 ab | 5.8 ab | 28.4 | (−) |

TABLE 2

| Fruit Brown-rot Disease Scores | | | |
|---|---|---|---|
| Genotype | Lesion Diameter (mm) | Proportion Infected | Disease Severity |
| Carson | 16.25 | 0.90 | 9.5 |
| Kader | 8.60 | 0.60 | 5.2 |
| Goodwin | 11.22 | 0.83 | 5.8 |
| Andross | 14.0 | 0.67 | 9.3 |

TABLE 2-continued

| Fruit Brown-rot Disease Scores | | | |
|---|---|---|---|
| Genotype | Lesion Diameter (mm) | Proportion Infected | Disease Severity |
| Ross | 21.53 | 0.90 | 16.9 |
| Dr.Davis | 14.6 | 0.44 | 6.1 |

TABLE 3

| Flesh Browning and PPO Activity | | |
|---|---|---|
| Genotype | Flesh browning (CIE L* value - % loss over 12 h) | PPO activity (mAbs/mi |
| Carson | 0.04 | 156 |
| Kader | 0.03 | 178 |
| Dixon | 0.41 | 242 |
| Goodwin | 0.22 | 20 |
| Andross | 0.40 | 383 |
| Ross | 0.35 | 193 |

TABLE 4

| Fruit Flesh Firmness | | | | |
|---|---|---|---|---|
| | Ave. firmness at Tree Ripe | STD | Ave. firmness at Tree Ripe + 7 d | STD |
| Kader | 7.7 | 2.8 | 6.8 | 1.6 |
| Dixon | 6.3 | 2.0 | 4.9 | 0.8 |

What we claim is:

1. A new and distinct variety of peach tree designated 'Kader' as shown and described herein.

* * * * *